US00PP32950P3

(12) United States Plant Patent
Knapp et al.

(10) Patent No.: US PP32,950 P3
(45) Date of Patent: Apr. 6, 2021

(54) STRAWBERRY PLANT NAMED 'UCD WARRIOR'

(50) Latin Name: ***Fragaria* x *ananassa* Duchesne**
Varietal Denomination: UCD Warrior

(71) Applicant: The Regents of the University of California, Oakland, CA (US)

(72) Inventors: Steven J. Knapp, Davis, CA (US); Glenn S. Cole, Davis, CA (US); Douglas V. Shaw, Davis, CA (US); Kirk D. Larson, Santa Ana, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/501,373

(22) Filed: Apr. 1, 2019

(65) Prior Publication Data

US 2019/0380244 P1 Dec. 12, 2019
US 2020/0187401 P9 Jun. 11, 2020

Related U.S. Application Data

(60) Division of application No. 15/932,994, filed on Jun. 7, 2018, which is a continuation of application No. 15/530,135, filed on Dec. 6, 2016, now abandoned, which is a continuation of application No. 14/545,653, filed on Jun. 3, 2015, now abandoned.

(60) Provisional application No. 61/999,632, filed on Jul. 30, 2014, provisional application No. 61/997,548, filed on Jun. 4, 2014.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ..... A01H 6/7409
See application file for complete search history.

*Primary Examiner* — Anne Marie Grunberg
(74) *Attorney, Agent, or Firm* — Kilpatrick Townsend & Stockton LLP

(57) ABSTRACT

'UCD Warrior' is a short-day cultivar of a strawberry plant that is highly resistant to *Fusarium* wilt; exhibits resistance to *Verticillium* wilt and *Macrophomina*; and produces high yields of high quality, long shelf-life fruit.

6 Drawing Sheets

Genus and species: The strawberry cultivar of this invention is botanically identified as *Fragaria* x *ananassa* Duchesne.

Variety denomination: The variety denomination is 'UCD Warrior'.

BACKGROUND OF THE INVENTION

This invention relates to a new and distinct short-day strawberry cultivar designated as 'UCD Warrior', which originated from a cross performed in the winter of 2008 between proprietary germplasm parents 05C165P001 (unpatented) and 04C076P004 (unpatented). Seeds of the cross were harvested from greenhouse-grown plants in the spring of 2008 and germinated in June 2008. Seedlings were transplanted to a greenhouse in July 2008 and transplanted to the field in October 2008. 'UCD Warrior' was selected and clones were first harvested in 2009. 'UCD Warror' has been asexually propagated since 2009.

The plant of this selection was originally designated '08C138P003' (also represented as 8.138-3) and later called '16SD034' or 'UC34' for evaluation in field trials.

BRIEF SUMMARY OF THE INVENTION

'UCD Warrior' is a short-day strawberry cultivar selected for increased marketable fruit yield, earliness, and resistance to *Fusarium* wilt, *Verticillium* wilt, and *Macrophomina*.

'UCD Warrior' consistently produces more marketable fruit per hectare than 'San Andreas' (U.S. Plant Pat. No. 19,975) and 'Petaluma' (U.S. Plant Pat. No. 26,683). The cumulative marketable fruit yields of 'UCD Warrior' are slightly less than 'Fronteras' (U.S. Plant Pat. No. 26,709). 'UCD Warrior' exhibits some resistance to *Macrophomina* whereas 'Fronteras', 'Petaluma', 'San Andreas', and 'UCD Victor' (U.S. Plant patent application Ser. No. 16/501,372) are highly susceptible to *Macrophomina*. 'UCD Warrior' exhibits increased *Fusarium* resistance compared to parent 05C165P001, and is more compact and exhibits increased *Macrophomina* resistance. compared to parent 04C076P004.

'UCD Warrior' was genotyped with a 35,000-SNP array (Hardigan et. al., *Plant Genome* 11:180049, 2018). The variety has a unique DNA profile compared to 'UCD Victor', 'Fronteras', 'Petaluma' and 'San Andreas'. The pairwise genetic distances between 'UCD Warrior' and 'UCD Victor', 'Fronterase', 'Petaluma' and 'San Andreas' are estimated to be 0.267, 0.257, 0.273, and 0.329, respectively based on the 35,000-SNP genotype analysis. 'UCD Warrior' also has a unique DNA profile compared to each of its parents, proprietary germplasm varieties 05C165P001 and 04C076P004.

'UCD Warrior' is maintained by annual asexual propagation by stolons in Winters, Calif.

BRIEF DESCRIPTION OF THE DRAWINGS

The colors in the photograph are depicted as nearly true as is reasonably possible to obtain in color reproductions of this type.

DETAILED DESCRIPTION OF THE INVENTION

Fruit Production

Figure 1:
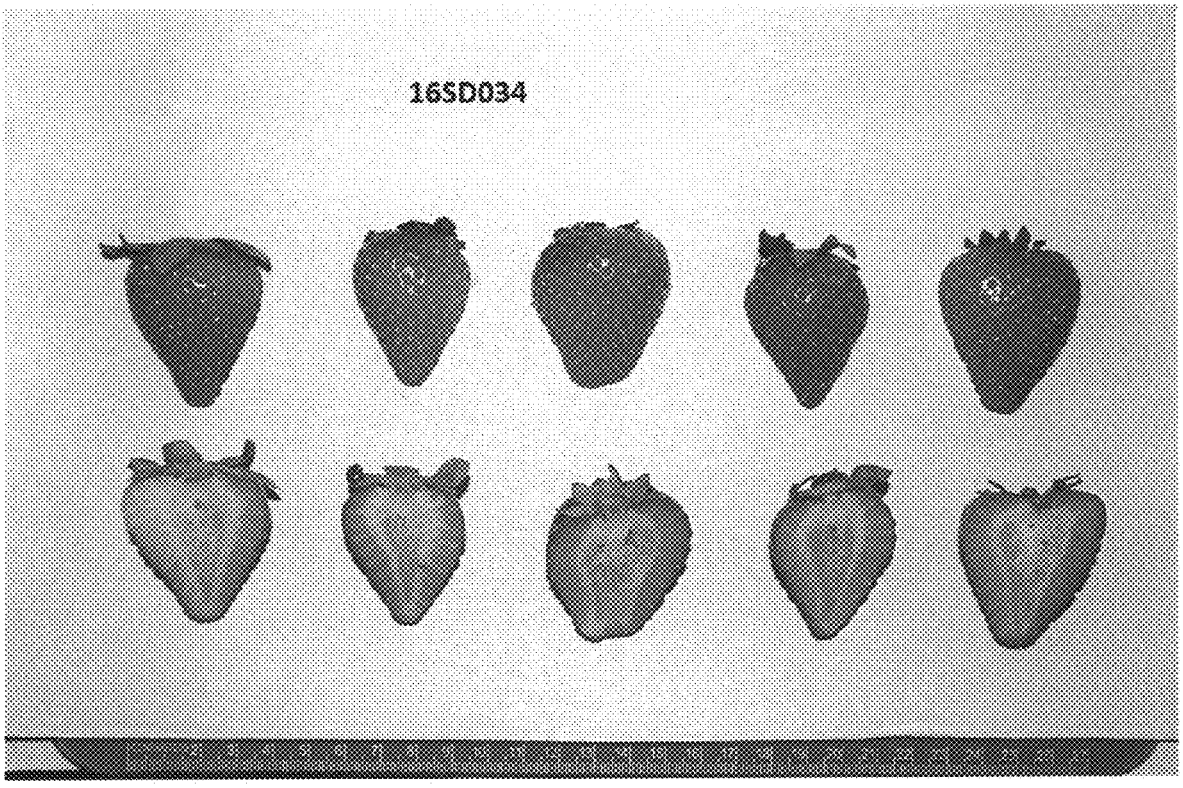
FIG. 1 shows fruit of 'UCD Warrior' in cross-section.
Figure 2:
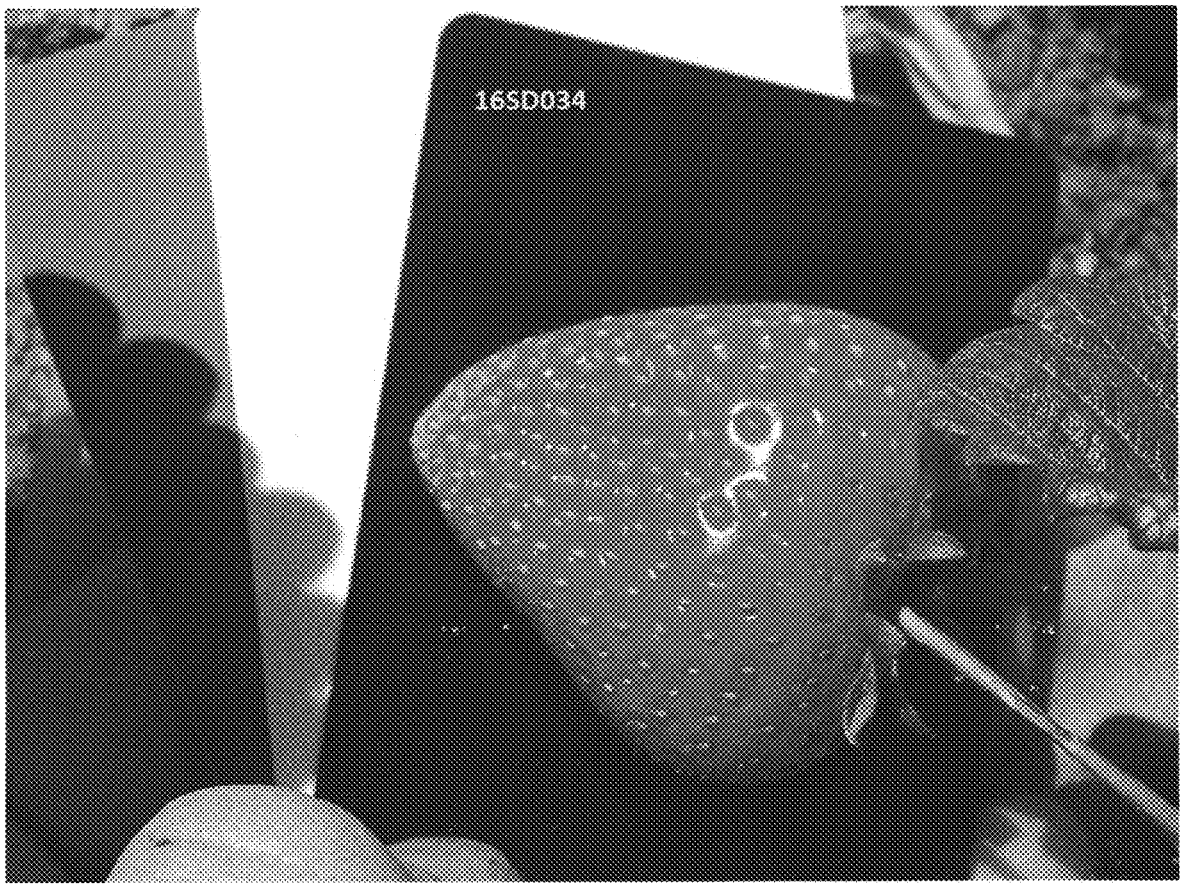
FIG. 2 illustrates color of the fruit.
Figure 3:
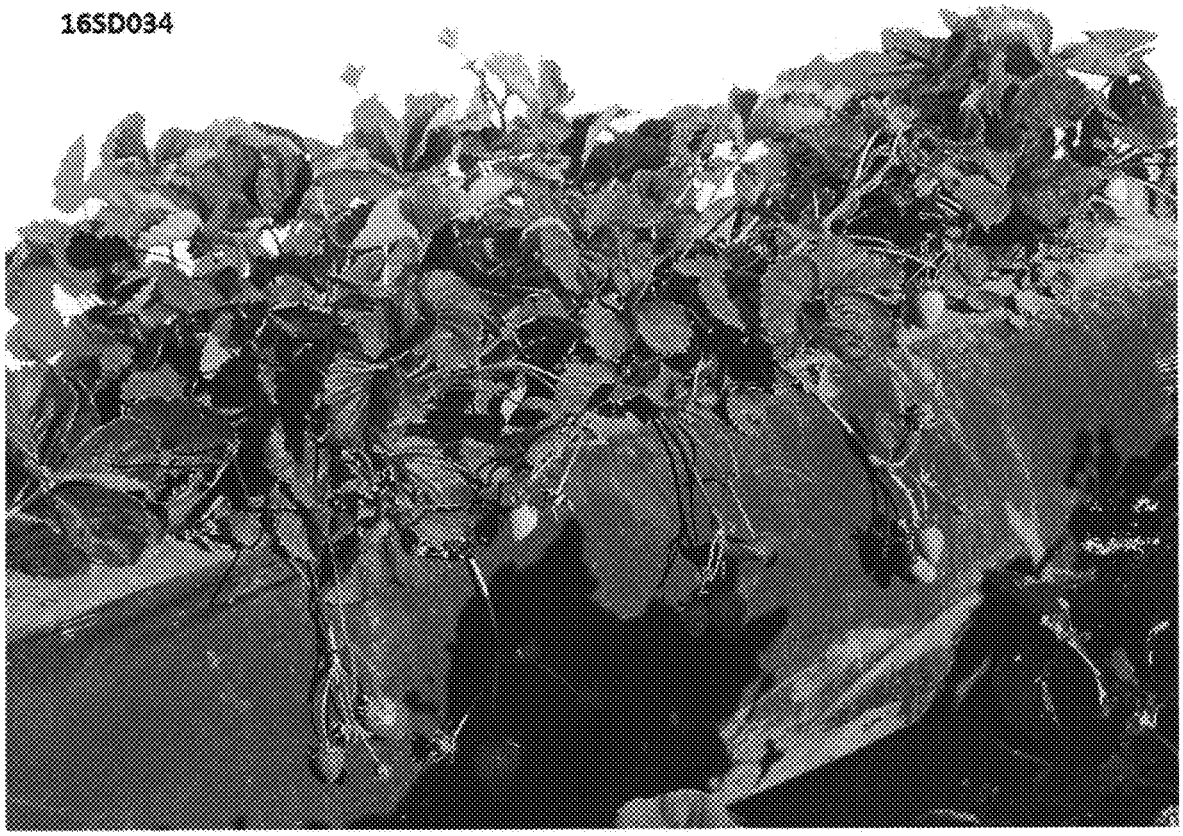
FIG. 3 depicts general plant and fruiting characteristics of 'UCD Warrior'.
Figure 4:
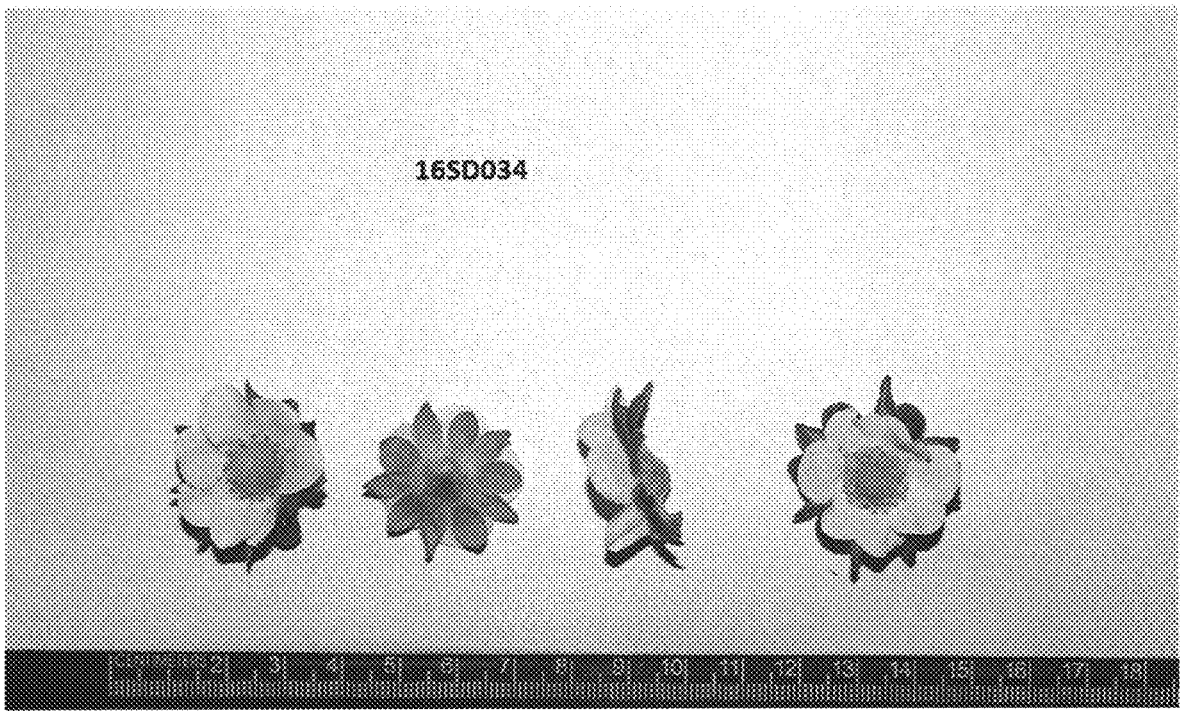
FIG. 4 shows representative flowers of the plant.
Figure 5:
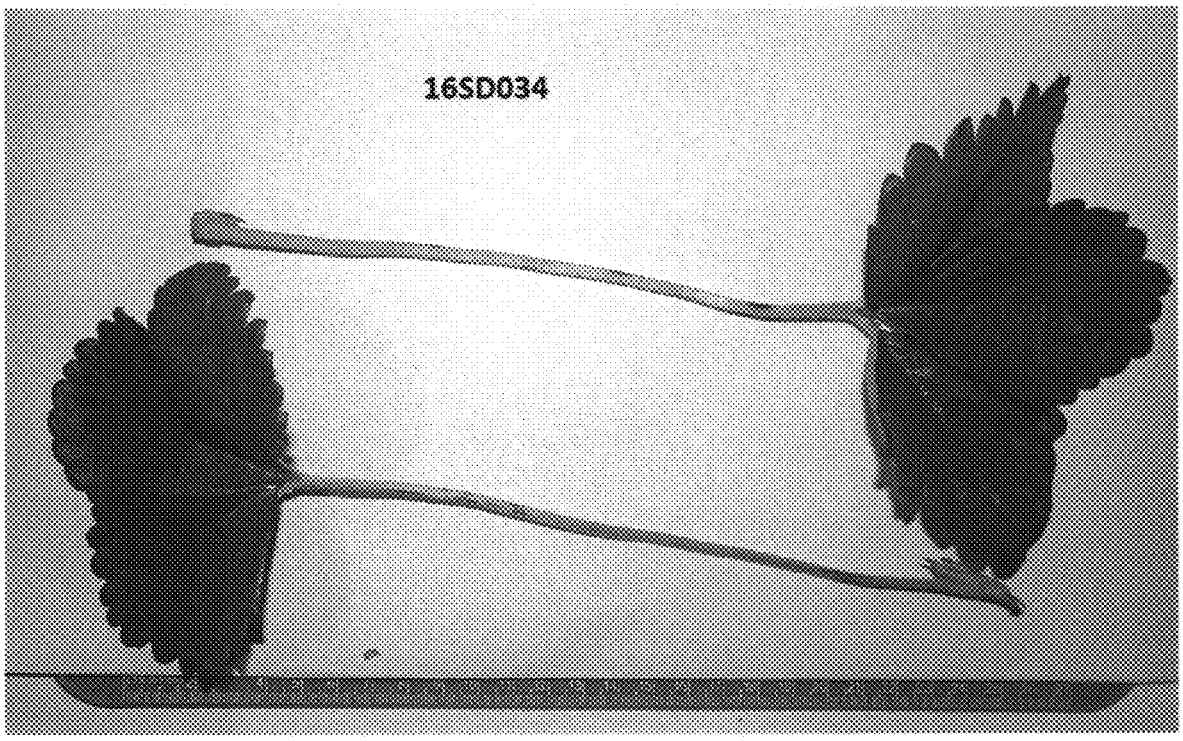
FIG. 5 shows representative leaves of the plant.
Figure 6:
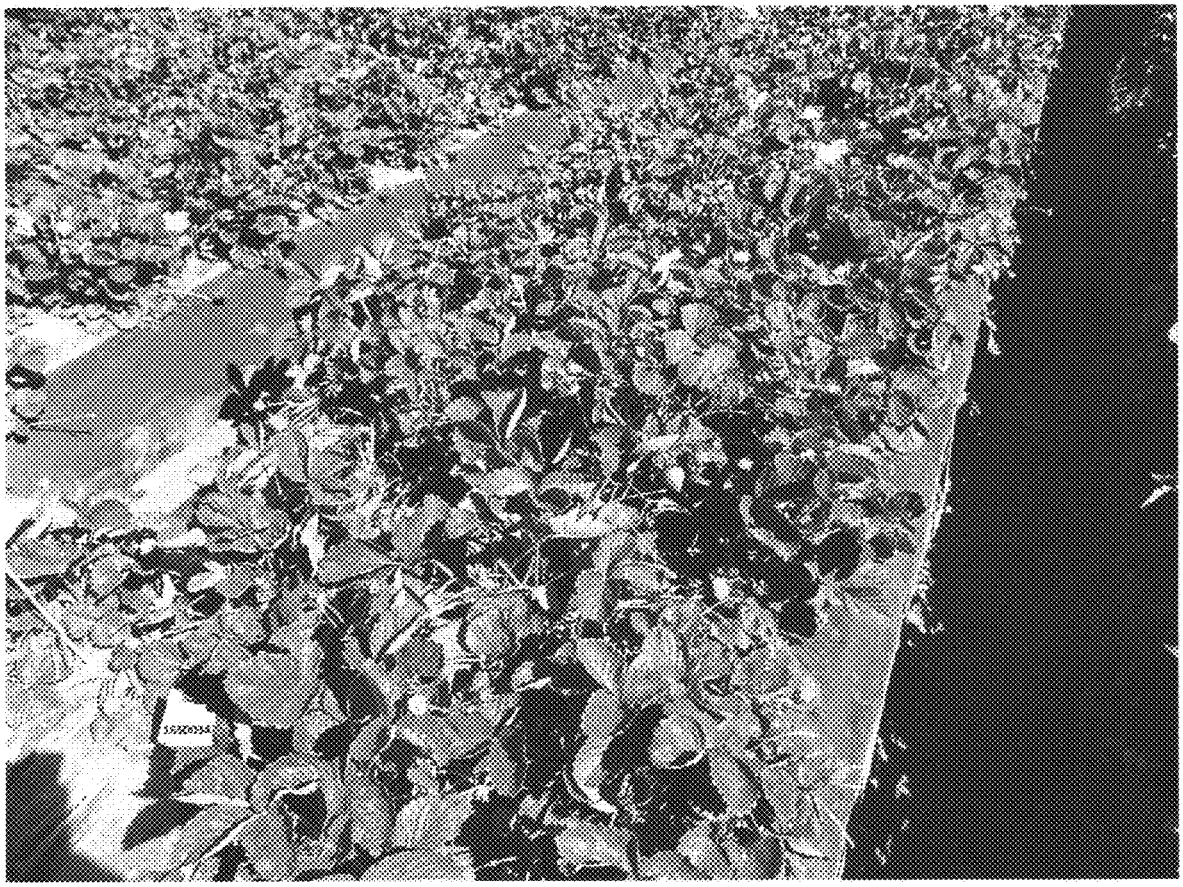
FIG. 6 depicts plant habit.

'UCD Warrior' and comparison cultivars were asexually propagated in high-elevation nurseries in Dorris and Mcdoel, Calif. for field testing in 2015-2016, 2016-2017, and 2017-2018. Clones were harvested according to commercial planting schedules, which were calibrated by the number of chill hours required for optimum production in Oxnard, Calif. and Santa Maria, Calif.

'UCD Warrior' and comparison cultivars were tested in replicated small-plot (24 plants/plot) yield trials in 2015-2016 in Oxnard and Santa Maria, Calif. Cultivar testing in the small-plot yield trials was performed as follows. Fruit was harvested once or twice per week over the spring and summer growing season: Dec. 24, 2015 to Jun. 2, 2016 in Oxnard, Calif. (49 harvests) and Feb. 14, 2016 to Jun. 27, 2016 in Santa Maria, Calif. (34 harvests). 'UCD Warrior' was selected on the basis of fruit firmness, appearance, size, flavor, and cumulative marketable fruit yield for a second year (2016-17) of replicated testing in small-plot yield trials in Oxnard and Camarillo, Calif. (Tables 1-2). Fruit was harvested once or twice per week over the growing season: Dec. 10, 2016 to Apr. 27, 2017 in Oxnard, Calif. (36 harvests) and Dec. 14, 2016 to May 15, 2017 in Camarillo, Calif. (26 harvests). To highlight differences among cultivars, the yield data were displayed in four ways: (a) per plant yields for individual harvests for each location×year combination for 'UCD Warrior', 'Fronteras', 'Petaluma', and 'San Andreas'; (b) per plant cumulative marketable yields for 'UCD Warrior', 'Fronteras', 'Petaluma', and 'San Andreas'; (c) per plant cumulative marketable yields for the cultivars tested in Oxnard and Santa Maria in 2015-16; and (d) per plant cumulative marketable yields tested in both years and locations.

Table 1 shows cumulative marketable yield (g/plant) for 'UCD Warrior' compared to that for 'Fronteras', 'Petaluma', and 'San Andreas' in small-plot yield trials in Oxnard and Santa Maria, Calif. in 2015-2016; and Oxnard and Camarillo, Calif. in 2016-2017.

Table 2 shows statistical significance of differences between cumulative fruit yield and fruit weight for 'UCD Warrior' and 'Fronteras', 'Petaluma', and 'San Andreas' in small-plot yield trials in Oxnard and Santa Maria, Calif. in 2015-2016; and Oxnard and Camarillo, Calif. in 2016-2017.

TABLE 1

Least-square means for cumulative marketable yield tested (g/plant).

| Cultivar | Oxnard 2015-16 | Santa Maria 2015-16 | Camarillo 2016-17 | Oxnard 2016-17 | Yield across Locations and Years (g/plant) |
|---|---|---|---|---|---|
| UCD Warrior | 818.9 | 818.1 | 786.6 | 571.0 | 749.2 |
| Petaluma | 652.7 | 669.3 | 447.2 | 519.8 | 572.8 |
| San Andreas | 700.3 | 648.4 | 428.2 | 448.8 | 557.9 |
| Fronteras | 918.5 | 806.4 | 786.6 | 738.8 | 811.8 |

TABLE 2

Statistical significance (Pr > F) of differences between least square means for cumulative fruit yield (g/plant) and fruit weight (g/fruit) for 'Fronteras', 'Petaluma', and 'San Andreas' tested in small-plot yield trials in Oxnard and Santa Maria, CA in 2015-2016; and Oxnard and Camarillo, CA in 2016-2017.

| | Yield (g/plant) | | Fruit Weight (g/fruit) | |
|---|---|---|---|---|
| Comparison | Estimate | Pr > F | Estimate | Pr > F |
| UCD Warrior-Fronteras | −62.6 | 0.2332 | −1.12 | 0.3332 |
| UCD Warrior-Petaluma | 176.5 | 0.0010 | −0.37 | 0.7492 |
| UCD Warrior-San Andreas | 191.4 | 0.0004 | 2.09 | 0.0734 |

There were significant differences among entries for cumulative marketable fruit yield ($p<0.0001$) and fruit weight ($p<0.0001$). Entry×environment interaction effects were significant for cumulative marketable fruit yield ($p<0.0001$) and fruit size ($p<0.0001$); however, entry rankings were fairly consisent and the best and worst performing cultivars were similar over locations and years (Tables 1-2). The broad-sense heritability for cumulative marketable fruit yield was 0.70 across locations and years. The broad-sense heritability for fruit weight was 0.59 across locations and years.

The cumulative marketable fruit yields of 'UCD Warrior' were significantly greater than 'Petaluma' ($p=0.001$) and 'San Andreas' ($p=0.004$) and not significantly different from Fronteras ($p=0.23$) across years and locations (Tables 1 and 2). 'UCD Warrior' produced high yields early in the season.

There were no significant differences in fruit weight among the cultivars tested (least square mean differences across years and locations and associated p-values are shown in Table 2).

'UCD Warrior' was selected for advanced testing in large-plot yield trials (150 plants/plot) in 2017-2018 (Tables 3 and 4). Several traits factored into the selection: resistance to one or more soil-borne pathogens, described below; high cumulative marketable fruit yield; fruit appearance; and resistance to bruising and post-harvest deterioration caused by harvest, handling, and storage. The production systems for large-plot yield trials included: low-input organic (Ventura) and high-input fumigated (Oxnard, Camarillo, and Santa Maria). These trials provided fruit for quality and post-harvest analyses.

TABLE 3

Least-square means (LSMs) for firmness, soluble solids concentration (SS), and titratable acid concentration (TA) for 'UCD Warrior' and 'Fronteras' grown in four locations in 2017-18. LSMs were estimated from three harvest dates per location, one biological replication per harvest date, 12 sub-samples per harvest date for firmness, and three sub-samples per harvest date for SS and TA.

| Cultivar | Firmness (g force) | SS (%) | Titrable Acids (g/100 ml) | SS/TA |
|---|---|---|---|---|
| UCD Warrior | 283.9 | 8.5 | 0.73 | 11.8 |
| Fronteras | 293.3 | 8.6 | 0.71 | 12.1 |

TABLE 4

Statistical significance (Pr > F) of differences between least square means for fruit firmness (g force) for 'UCD Warrior' and 'Fronteras' tested in unreplicated large-plot yield trials in four locations in 2017-18.

| | Firmness | | SS/TA | |
|---|---|---|---|---|
| Comparison | Difference (g/force) | Pr > F | Difference | Pr > F |
| UCD Warrior-Fronteras | −9.4 | 0.6724 | −0.36 | 0.5069 |

To assess the quality of freshly harvested fruit, firmness (grams force), total soluble solids (SS) concentration, and titratable acid (TA) concentrations were measured from samples of fruit harvested on three dates from large-plot yield trials on farms in Oxnard, Camarillo, Ventura, and Santa Maria, Calif. in 2017-18 (Tables 3 and 4). Harvest dates were one month apart with one replication per harvest date, 12 sub-samples per replication for firmness, and three subsamples per replication for SS and TA. Firmness was quantified with a hand-held penetrometer measuring the grams of force needed to puncture the fruit. SS and TA concentrations were quantified with benchtop instruments. The SS to TA ratio provides a relative measure of sweetness.

The firmness of 'UCD Warrior' did not differ significantly from that of 'Fronteras', nor was the SS/TA ratio for 'UCD Warrior' significantly different from Fronteras (Tables 3 and 4).

To assess shelf-life, fruit weight (g/clamshell), SS, brightness (ordinal scale with 1=excellent to 5=unmarketable), liquid leakage (g/clamshell), and mold incidence (%) were quantified from samples of fruit harvested on two dates from each location with fruit stored under standard 4° C. conditions for 0, 7, and 14 days (Table 5). Harvest dates were one month apart with one replication per harvest date.

TABLE 5

Least-square means (LSMs) for fruit weight (g/clamshell), soluble solids concentration (SS), fruit brightness, liquid leakage, and mold formation for 'UCD Warrior' and 'Fronteras' grown in four locations in 2017-18 and stored for zero to 14 days postharvest. LSMs were estimated from two harvest dates per location.

| Cultivar | Days Post-Harvest | Weight (g/clamshell) | Soluble Solids (%) | Bright-ness | Liquid Leakage (g) | Mold (%) |
|---|---|---|---|---|---|---|
| UCD Warrior | 0 | 258.1 | 6.9 | 1.2 | 0.0 | 0.0 |
| UCD Warrior | 7 | 245.7 | 6.8 | 3.3 | 2.3 | 0.0 |

TABLE 5-continued

Least-square means (LSMs) for fruit weight (g/clamshell), soluble solids concentration (SS), fruit brightness, liquid leakage, and mold formation for 'UCD Warrior' and 'Fronteras' grown in four locations in 2017-18 and stored for zero to 14 days postharvest. LSMs were estimated from two harvest dates per location.

| Cultivar | Days Post-Harvest | Weight (g/clamshell) | Soluble Solids (%) | Bright-ness | Liquid Leakage (g) | Mold (%) |
|---|---|---|---|---|---|---|
| UCD Warrior | 14 | 230.9 | 7.1 | 3.8 | 3.2 | 2.7 |
| Fronteras | 0 | 294.3 | 7.3 | 1.0 | 0.0 | 0.0 |
| Fronteras | 7 | 281.6 | 7.1 | 3.5 | 0.8 | 0.0 |
| Fronteras | 14 | 267.4 | 7.7 | 4.3 | 3.0 | 4.8 |

'UCD Warrior' and 'Fronteras' maintained adequate marketability and visual appearance over 12-14 days of postharvest storage, the industry standard (Table 5). Fruit weight and brightness significantly decreased and liquid leakage and mold formation increased among cultivars as postharvest storage time increased, where brightness was measured on an ordinal 1 to 5 scale with 1=superior and 5=inferior (Table 5). The fruit weight decreases were significantly greater for 'UCD Warrior' than Fronteras ($p<0.0001$). Soluble solids concentrations were not significantly different between 'UCD Warrior' and 'Fronteras'.

Disease Resistance Evaluation

'UCD Warrior' and additional cultivars was screened for resistance to *Fusarium* wilt, *Verticillium* wilt, *Macrophomina*, and *Phytophthora* crown rot in Davis, Calif. field experiments between 2015 and 2018. These included 2015-16 and 2016-17 *Fusarium* wilt screening experiments with 480 to 960 entries, a 2015-16 *Macrophomina* experiment with 960 entries, 2016-17 and 2017-18 *Verticillium* wilt experiments with 480 to 960 entries, and a 2017-18 *Phytophthora* crown rot experiment with 480 entries. Entries were arranged in randomized complete blocks experiment designs with four single-plant replications per entry. The 2015-16 experiments were planted in virgin soil in Davis, Calif. The 2016-17 and 2017-18 experiments were planted in fumigated soils in Davis, Calif. For each experiment, plants were artificially inoculated with the respective pathogen and phenotyped for disease symptoms on an ordinal scale, where 1=highly resistant (symptomless), 2=resistant, 3=intermediate, 4=susceptible, and 5=highly susceptible (dead). Within each experiment, plants were phenotyped at six different time points to study changes in the phenotypic distributions and quantify the progression of disease symptoms over time.

'UCD Warrior' was highly resistant to *Fusarium* wilt (1.0 on scale) and heterozygous for $Fw_1$, a dominant resistance gene. The *Fusarium* wilt resistance score was not significantly different from the score for 'Fronteras' (1.1).

'UCD Warrior' was moderately resistant to *Verticillium* wilt (2.9 on scale), and was not significantly different from 'Fronteras' ($p=1.00$), which was also 2.9 on scale.

'UCD Warrior' was also moderately resistant to *Phytophthora* crown rot (2.9 on scale), and did not differ significantly from 'Fronteras' ($p=1.00$), also 2.9 on scale.

'UCD Warrior' was moderately resistant to *Macrophomina* (2.7 on scale) and was significantly more resistant to *Macrophomina* than 'Fronteras' ($p=0.014$), which was 4.3 on the resistance scale.

BOTANICAL DESCRIPTION

The following botanical descriptors are characteristic of 'UCD Warrior'. The descriptors were collected from two different sites in May 2017 in Santa Maria, Calif. Colors are designated with reference to The Royal Horticultural Society (R.H.S.) Colour Chart, Sixth Edition, 2015. The characteristics of 'UCD Warrior' may vary in detail, depending upon environmental factors and culture conditions.

Growth habitat: Semi-upright Plant height average of 27 cm. Plant spread average of 39 cm.
Density of foliage: Medium.
Vigor: Medium.
Position of inflorescence in relation to foliage: Same level.
Number of stolons: Average of 14.
Stolon, anthocyanin coloration: 61B.
Stolon, density of pubescence: Sparse.
Leaf size: Medium.
Leaf color: Adaxial 137B, Abaxial 138B.
Leaf blistering: Absent or weak.
Leaf glossiness: Medium glossy.
Leaf variegation: Absent.
Terminal leaflet, length in relation to width: Average of 75 mm long and 60 mm wide.
Terminal leaflet, shape of base: Obtuse.
Terminal leaflet, margin: Serrate to crenate.
Terminal leaflet, shape in cross section: Concave.
Petiole, length: Average of 8 cm.
Petiole, attitude of hairs: Horizontal.
Stipule, anthocyanin coloration: Core color 144D, Margin color 144A (absent or very weak).
Inflorescence, number of flowers: Many.
Pedicel, attitude of hairs: Horizontal.
Pedicel, anthocyanin coloration: 61B.
Flower diameter: Average of 25 mm.
Flower, arrangement of petals: Touching.
Flower, size of calyx: Calyx diameter average of 33 mm.
Color of calyx: 137A.
Flower stamen: Present.
Number of stamens per flower: Average of 24.
Number of sepals per flower: Average of 12.
Petal, length in relation to width: Equal, Average of 10 mm long and 10 mm wide.
Petal, color of upper side: NN155B.
Petal, color of lower side: Average of 6.
Number of petals per flower: Average of 6.
Fruit, length in relation to width: Average of 41 mm long and 32 mm wide.
Fruit size: Average of 26 grams through the season for both primary and secondary fruit.
Fruit shape: Conical.
Fruit, difference in shape of terminal and other fruits: None or very slight.
Fruit color: N34A.
Fruit, evenness of color: Even or very slightly uneven.
Fruit glossiness: Medium.
Fruit, evenness of surface: Even or very slightly uneven.
Fruit, width of band without achenes: Absent or very narrow.
Fruit, positions of achenes: Below surface.
Acene color: 4A.
Fruit, position of calyx attachment: Inserted.
Fruit, attitude of sepals: Upwards.
Fruit, diameter of calyx in relation to fruit diameter: Same size.
Fruit, adherence of calyx: Medium.
Fruit firmness: Firm.
Fruit, color of flesh (excluding core): 34B.
Fruit, color of core: 41D.
Fruit cavity: Average of 10.4 mm.
Time of beginning of flowering: Early, starts in January to May.
Time of beginning of fruit ripening: Early, starts in February to June.
Type of bearing: Not remontant.

PLANT AND FOLIAGE COMPARISONS

Fruiting plants of 'UCD Warrior' are shorter than 'Fronteras' and 'Petaluma', but taller than 'San Andreas'. The spread is wider than all 3 of the comparative cultivars. Leaves (including petioles) for 'UCD Warrior' are shorter than 'Fronteras' and 'San Andreas', but more similar to 'Petaluma'. Color for the upper and lower levels of the leaves of 'UCD Warrior' are a similar green color as 'Petaluma', but darker green than 'Fronteras' and 'San Andreas'. Serrations at midseason are more pointed than 'Fronteras' and more similar in shape and number to 'Petaluma' and 'San Andreas'. The stipule length of 'UCD Warrior' is similar to 'Petaluma' but shorter than 'Fronteras' and 'San Andreas'. Stolon production of 'UCD Warrior' is greater than 'San Andreas', but less than for 'Fronteras' and 'Petaluma'.

FLOWERING AND FRUITING COMPARISONS

'UCD Warrior' is similar to other California short day cultivars (e.g., 'Fronteras' and 'Petaluma') in that it will flower over an extended period into spring and early summer, given appropriate temperature and horticultural conditions. With most planting treatments, 'UCD Warrior' flowers slightly earlier than 'Fronteras', but slightly later than 'Petaluma' and 'San Andreas'. The primary flowers for 'UCD Warrior' are similar in size to 'Fronteras' but are larger than flowers for 'Petaluma' and 'San Andreas'. The calyx is distinctly larger relative to the corolla on the primary fruit. The sepals for 'UCD Warrior' are longer than 'Fronteras', but shorter than 'Petaluma' and 'San Andreas'. Sepal width is similar to 'Fronteras' and 'San Andreas' but distinctly narrower than Petaluma. The calyx of 'UCD Warrior' is variable (flat to slightly reflexed) more similar to 'Fronteras' and 'San Andreas', less reflexive than 'Petaluma'. The fruit shape of 'UCD Warrior' can vary through the season, but is generally a short to medium conic fruit similar to the fruit of Petaluma, as compared to the more medium conic fruit of 'Fronteras' and the long conic fruit of 'San Andreas'. External fruit color for 'UCD Warrior' is similar to both 'Fronteras' and 'Petaluma'. The internal fruit color of 'UCD Victor' is similar to 'Petaluma', but darker than 'Fronteras'.

Achenes of 'UCD Warrior' are even to slightly indented in the fruit, similar to the fruit of 'San Andreas' but less indented than 'Fronteras' and 'Petaluma'.

What is claimed is:

1. A new and distinct cultivar of strawberry plant having the characteristics substantially as described and illustrated herein.

* * * * *